United States Patent [19]

Sacco

[11] Patent Number: 5,059,173
[45] Date of Patent: Oct. 22, 1991

[54] IV APPARATUS

[76] Inventor: John J. Sacco, 202 Sedgwick Dr., Syracuse, N.Y. 13203

[21] Appl. No.: 557,388

[22] Filed: Jul. 28, 1990

Related U.S. Application Data

[63] Continuation-in-part of Ser. No. 503,937, Apr. 4, 1990, abandoned.

[51] Int. Cl.$^5$ .............................................. A61M 5/14
[52] U.S. Cl. ....................................... 604/80; 604/83; 604/246
[58] Field of Search ....................... 604/80, 81, 82, 83, 604/246, 251, 254, 258

[56] References Cited

U.S. PATENT DOCUMENTS

| | | |
|---|---|---|
| 3,841,307 | 10/1974 | Friedell . |
| 4,037,599 | 7/1977 | Raulerson . |
| 4,096,860 | 6/1978 | McLaughlin . |
| 4,186,740 | 2/1980 | Guerra . |
| 4,252,116 | 2/1981 | Genese et al. ...................... 604/83 X |
| 4,256,105 | 3/1981 | Leahey et al. ......................... 604/81 |
| 4,257,416 | 3/1981 | Prager . |
| 4,258,712 | 3/1981 | Harms et al. .......................... 604/81 |
| 4,312,342 | 1/1982 | Chittenden . |
| 4,430,074 | 2/1984 | Mooring . |
| 4,490,135 | 12/1984 | Troutner . |
| 4,526,568 | 7/1985 | Clemens et al. . |
| 4,573,974 | 3/1986 | Ruschke ............................... 604/81 |
| 4,776,837 | 10/1988 | Kopp . |
| 4,842,588 | 6/1989 | Jones . |
| 4,915,689 | 4/1990 | Theeuwes . |

OTHER PUBLICATIONS

Kendall McGraw Product Catalog, pp. B-4, B-6 and B-7, Jul. 1, 1990.
Baxter Laboratories sales brochure dated 1/1/89, p. VII-1.
American Journal of Hospital Pharmacy article, vol. 29, Jun. 1972, pp. 486-490.

*Primary Examiner*—John D. Yasko
*Attorney, Agent, or Firm*—Wall and Roehrig

[57] ABSTRACT

The gravity flow fluid path for administering IV fluids to a patient is disclosed in which multiple IV fluids can be delivered at different flow rates to the patient without having to replace the administration set up.

16 Claims, 1 Drawing Sheet

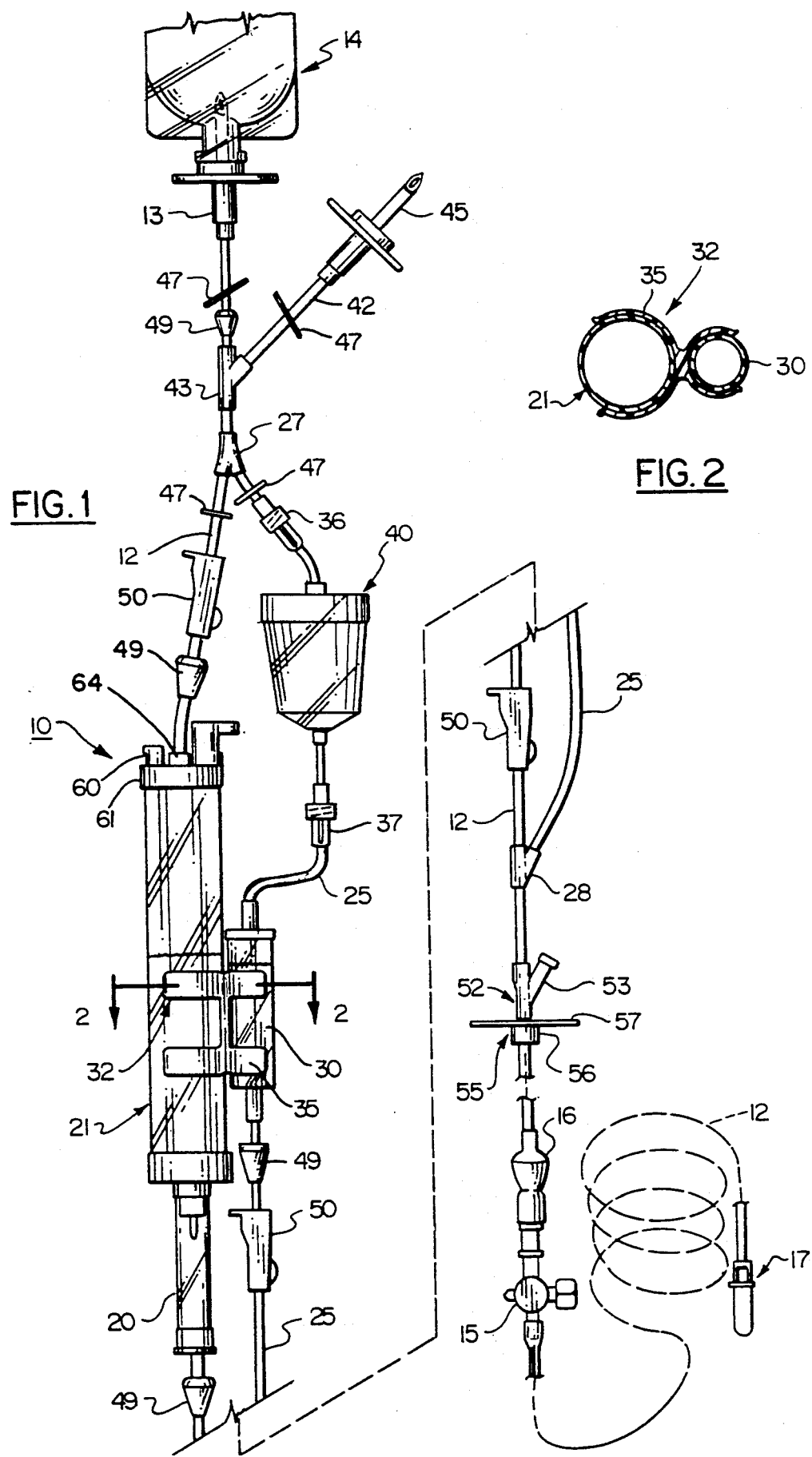

IV APPARATUS

This application is a continuation-in-part of U.S. patent application Ser. No. 503,937, filed Apr. 4, 1990 for IV APPARATUS now abandoned.

BACKGROUND OF THE INVENTION

This invention relates to a multi-purpose gravity operated fluid path for administering fluids intravenously to a patient.

Solution administration devices or fluid paths used for delivering intravenous (IV) fluids to a patient are well-known in the art. These devices are sometimes referred to simply as IV sets and generally include a tubular flow line having a capped spike at the upper end that is capable of being inserted into an IV solution bag and a catheter tip at the lower end for infusing fluid into a patient's vein. The flow line also includes a flow regulator, typically in the form of a drip chamber, which determines the maximum rate of flow that can be passed through the line and thus the maximum amount of fluid that will be administered to the patient over a given period of time. One or more adjustable roller clamps are typically attached to the line above and below the drip chamber for either closing off the line completely or further regulating the flow. A graduated burette is generally placed in series flow relationship with the drip chamber to allow the attending health care worker to accurately monitor the amount of fluid administered to the patient.

During most normal procedures, IV fluids are administered continuously over extended periods of time at relatively low flow rates. Oftentimes, however, a situation, such as the need for surgery, will arise where a continuous low flow fluid path will not satisfy the needs of the patient. Under these conditions, the low flow administration set-up is removed and replaced with a high-flow set-up. When the patient's special needs are satisfied, the high-flow administration set-up is removed and once again replaced with a new low-flow set-up.

This repeated setting up and taking down of the IV system is a time consuming procedure which wastes substantial amounts of health care time. This loss of time, particularly during emergency procedures, can increase the patient's risk factor. In light of the fact that an IV administration set-up can be used only once, the use of multiple set ups during a single procedure can be relatively costly. More importantly, the hospital must inventory a reasonably large amount of this type of equipment to meet the needs of its patients. Large inventories are space consuming and require a good deal of time and effort to stock and control. The disposal of used administration sets is also causing environmental problems which are now becoming more and more pronounced. Frequent IV starts also increase the risk of infection to the patient and any reduction in the number of starts will be of an immediate benefit to both patient and health care workers alike.

Frequently, a piggy-back arrangement is used to administer medication or blood through the injection port of any intravenous administration set. In this arrangement, a mini-bag, which is attached to a high flow or low-flow drip chamber, is inserted directly into the main flow line through an injection port located below the primary or low-flow drip chamber. During this procedure, the primary IV bag is lowered and the mini-bag raised to a higher elevation thereby allowing the secondary fluid to be administered by gravity through the injection port. Although this piggy-back arrangement works well in practice, it nevertheless does have certain disadvantages. The equipment takes time to set up and must be closely monitored, again resulting in the excessive use of valuable health care time. Typically, most patients require more than one secondary infusion and, as a result, the main fluid path will be invaded repeatedly. This, of course, increases the risk of infection. The needle used to invade the fluid path also poses a constant danger to the attending health care worker. Unless extreme care is exercised, the attending worker can puncture him or herself with the needle during the injection procedure. The initial wound itself may not be dangerous, however, puncture wounds provides a means by which blood-borne infections can be acquired.

OBJECTS AND SUMMARY OF THE INVENTION

It is therefore an object of the present invention to improve flow paths used to administer IV fluids to a patient.

A further object of the invention is to conserve valuable health care time when administering IV fluids.

A still further object of the present invention is to lessen the patient's risk when undergoing medical procedures involving the administration of IV fluids.

Another object of the present invention is to reduce the amount of equipment required to administer IV fluids to a patient who may require frequent changes in medication and dosages.

It is yet another object of the present invention to reduce the cost involved in administering IV fluids to a patient.

Still another object of the present invention is to reduce the amount of IV equipment that must be disposed of by a health care facility.

While a further object of the present invention is to reduce the amount of inventory that must be kept on hand by a health care facility.

Yet a further object of the present invention is to protect health care workers from potentially dangerous needle punctures by reducing the number of times an existing flow path must be invaded by a needle.

A further object of the present invention is to provide an attending physician with greater flexibility when administering IV fluids to a patient.

Another object of the present invention is to reduce the number of IV starts to safely satisfy a patient's needs.

These and other objects of the present invention are attained by means of an IV administration set-up that includes a main flow line having a capped spike for receiving an IV bag at the top end thereof and a needle unit at the bottom end thereof for injecting fluids into a patient. The main flow line has a first drip chamber mounted therein which is capable of administering fluids at a first flow rate. A shunt line is placed in the main flow line which bypasses the first drip chamber. A second drip chamber is mounted in the shunt line that is capable of administering fluids at a second flow rate. Clips and/or clamps are used to selectively open and close the lines to route IV fluids through a selected one of the two available drip chambers. An auxiliary line may also be provided which enters the main flow line above the upper shunt line entry point. The auxiliary line also contains a capped spike at its proximal end for receiving a second IV fluid bag. Additional clips and/or clamps are contained in the lines for selectively connecting one of the two available IV bags in fluid flow communication with the main flow line.

As can be seen, this multi-fluid, multi-flow arrangement provides the attending health care worker with a great deal of flexibility when administering fluids to a patient without the need of breaking down and replacing the solution administering set-up or repeatedly invading the equipment with potentially dangerous needle punctures.

BRIEF DESCRIPTION OF THE DRAWINGS

For a better understanding of these and other objects of the present invention, reference will be made to the following detailed description of the invention which is to be read in conjunction with the following drawings, wherein:

FIG. 1 is a side elevation showing a gravity operated flow path for administering IV fluids to a patient which embodies the teachings of the present invention, and FIG. 2 is a sectional view taken along lines 2—2 in FIG. 1.

DETAILED DESCRIPTION OF THE INVENTION

Referring now to the drawings there is illustrated a gravity operated flow path, generally referenced 10, which embodies the teachings of the present invention. The flow path contains a main flow line 12 that is made up of sections of flexible, clear plastic tubing. The top end of the main flow line is equipped with a capped spike 13 of conventional design that is capable of penetrating an IV fluid bag 14 thereby enabling the fluid contained in the bag to freely enter the main flow line. Although not shown, the IV fluid bag is furnished with a strap by which the bag, and thus the flow path set-up, is suspended from a suitable hanger. The bag is supported at an elevated position so that the IV fluids contained therein can flow under the influence of gravity downwardly through the flow path. The lower end of the main flow line is equipped with a three-way stopcock 15, a bubble flush 16, and a catheter tip 17, all of which are conventional devices that are well-known and used in the art.

A first primary drip chamber 20 is mounted in the main flow line that serves to regulate the rate of fluid flow that can pass through the line and thus be administered to the patient. In this embodiment of the invention, a mini-drip chamber is employed to administer IV fluids to the patient at a relatively low flow rate continuously over a long period of time. The mini-drip chamber is placed in series with a burette 21 that has a vertically disposed graduated scale (not shown) which allows an attending health care worker to accurately monitor the patient's fluid intake. Drip chamber and burette combinations of this type are sold commercially by Kendall McGaw, Inc. of Sabana Grande, Puerto Rico under the trade name Metriset.

A shunt flow line 25 is placed in the main flow line to provide an alternate flow path around the mini-drip chamber and burette combination. The shunt line, again, is made up of sections of flexible, clear plastic tubing. The shunt line is connected at its upper end to the main flow line by a Y-connector 27 which is situated above the burette and at its lower end by a similar connector 28 situated below the mini-drip chamber. A secondary "adult" drip chamber 30 is mounted in the shunt line and is arranged to pass fluids at a relatively higher flow rate than the mini-drip chamber. In this embodiment of the invention, the adult drip chamber is supported on the larger burette by means of a resilient plastic support member 32 (FIG. 2). The support member can be conveniently snapped over both the adult drip chamber and the burette to hold the two in parallel vertical alignment as shown in FIG. 1. The support member can also be slidably positioned along the length of the burette to selectively change the elevation of the adult drip chamber if required.

A luer lock connector having a male member 36 and a female member 37 is placed in the shunt line above the adult drip chamber. The luer lock connector permits the shunt line to be separated so that a blood filter 40 or other IV related device can be operatively connected into the shunt line. As will become apparent from the disclosure below, the shunt line can be employed in the present system to rapidly infuse blood or selected medications into a patient without having to replace or disconnect the IV set-up. The luer lock arrangement also allows the blood filter to be periodically changed without disturbing the existing administration set-up. Typically, blood filters require changing after the administration of one to two units of blood. When fluids, other than blood, are being administered through the shunt line, the blood filter can be removed and the line rejoined by simply coupling together the two halves of the luer lock connector.

An auxiliary line 42 is also connected into the main flow line by means of Y-connector 43 located above the entry point of the shunt line. The distal end of the auxiliary line is also equipped with a second capped spike 45. By use of the capped spike 45, a unit of blood or a second IV bag (not shown) can be coupled in fluid flow communication with the main flow line. A pair of shut-off clips 47—47 are mounted in the main line and the auxiliary line directly above the connector 43. The clips can be operated to open one line and close the other so that fluids from a selected one of the two available IV bags can be routed into the upper section of the main flow line. A one-way valve 49 is placed in the main line above connector 43 to prevent fluids from auxiliary line 42 from backing up into the upper section of the main line.

A similar pair of shut-off clips 47—47 are mounted in the main line and the shunt line immediately below connector 27. Again, the clips can be selectively opened and closed to route IV fluids from one of the two available IV bags into either the main line or the shunt line. Accordingly, the attending health care worker, at his or her option, can select one of the two available fluids for administration, and additionally the desired administration rate can be selected without having to break down or invade existing set-up. Accordingly, changes and dosages in fluids can be made rapidly and safely. This, of course, reduces the risk to the patient and reduces the amount of IV equipment needed to satisfy a patient's needs during various procedures. In short, the present apparatus provides an immediate benefit to everyone in the health care chain, including patients, medical workers, and care facility administrators.

Referring once again to FIG. 1, a one-way valve 49 is positioned in the flow lines immediately below each drip chamber to prevent fluids from moving upwardly in the lines and thus possibly mixing one fluid with another. In most cases, this reverse flow is not a problem because of the gravity flow arrangement. However, the valve will provide for added safety during the administration of fluids. Adjustable roller clamps 50—50 are also mounted at strategic positions within the main flow line and the shunt flow line. These roller clamps are operable to further control the flow of fluids through the lines or alternatively shut down the lines completely as may be required.

An injection port 52 is mounted in the main flow line directly below the lower shunt connector 52. The injection port contains a rubber tipped arm 53 through which a needle can be inserted thereby allowing further fluids to be introduced directly into the main flow line for rapid infusion into the patient. As noted above, it is not uncommon for a health care worker to puncture him or herself with the needle while attempting to pass it into the injection port. This is particularly true in emergency situations where time is important. The present device is provided with a molded circular shield 55 that surrounds the main flow line directly below the injection port. The shield includes a hub 56 that embraces the flow line without crimping it and a radially expanded flange 57 mounted upon the hub. When injecting a fluid into the injection port, the health care worker simply grasps the line below the shield with one hand, and passes the needle through the rubber tip port with the other hand. In the event the needle slips from the port, it will strike the expanded flange 57, rather than the worker's hand, thus protecting the worker from a potentially dangerous puncture wound.

The apparatus of the present invention can also be adapted to simultaneously administer two separate fluids through the catheter. In this operation, the burette is filled with a desired amount of a first fluid and the shunt line arranged to administer a second fluid from one of the available IV bags. The clamp 50 in the main flow line below the burette drip chamber combination is then opened to allow the first fluid to be administered along with the second fluid.

The burette contains an air vent 60 mounted in the top wall 61 thereof which can be selectively opened when the mine drip chamber is in use. Although not shown, a flapper valve is also located over the lower outlet of the burette which automatically closes when the liquid in the burette becomes depleted thereby preventing air from entering the mini-drip chamber. With the air vent opened a positive head pressure is exerted upon the fluid in the burette to provide for an ever and continuous flow of fluid through the mini-drip chamber. As noted above, the two strategically placed one-way check valves 49—49 positioned beneath each drip chamber permits non-competitive gravity-fed flow to be maintained for two different types of fluids Accordingly, various combinations of fluids such as medications, blood, IV solution and the like can be brought to the IV catheter at junction 28 at various desired flow rates.

The adult drip chamber can be used for the rapid infusion of fluids when required by the health care worker. There are set up arrangements, therefore, where air can be drawn through the air vent 60 upwardly through line 12, connector 27 and thus pass into the shunt line 25, thus posing a problem. To avoid this problem, a one-way check valve 49 is placed in the primary flow line 12 immediately above the inlet 64 to the burette. The valve functions to permit fluid to flow—under the influence of gravity from the supply bag or bottle, into the burette, but prevents fluids, including air, from moving in the opposite direction. Accordingly, air is thus prevented from being drawn into the shunt line.

While this invention has been explained with reference to the structure disclosed herein, it is not confined to the details as set forth and this application is intended to cover any modifications and changes as may come within the scope of the following claims.

What is claimed is:

1. A gravity flow fluid path for administering fluids intravenously to a patient that includes a main flow line having a penetrating means at the top end of said line for coupling said line to a fluid container, and an injection means at the bottom end of said line for intravenously introducing fluid to a patient, a mini-drip chamber mounted in said main flow line for administering fluids passing through said mini-drip chamber at a medically low flow rate, a shunt flow line connected into the main flow line by an upper connector located above said first regulating means and by a lower connector located below said first regulating means, An adult drip chamber mounted in said shunt flow line for administering fluids passing through said adult drip chamber at a medically high flow rate, and a first control means associated with said lines that is operable to selectively route fluid in transit through said mini-drip chamber and said adult drip chamber, a second control means associated with said lines that is operable to selectively route one fluid or two fluids concurrently through said lines.

2. The apparatus of claim 1 that further includes a second spike means connected into the main flow line above said upper connector by an auxiliary flow line for coupling said main flow line to a second fluid container, and clip means for selectively opening and closing the auxiliary flow line and the main flow line above said upper connector whereby fluid from a selected fluid container is fed to the main flow line.

3. The apparatus of claim 2 that further includes a one-way valve in the main line and in the shunt line below each of the flow regulating means to prevent fluid from moving upwardly in each line.

4. The apparatus of claim 1 that further includes an injection port means mounted in the main flow line below the lower connector.

5. The apparatus of claim 1 that further includes a blood filter means removably connected into said shunt flow line above said second flow regulator means.

6. The apparatus of claim 1 wherein one of said flow regulator means further includes a burette means mounted between the upper and lower connectors above the first flow regulator having graduations to permit monitoring the amount of fluid passing through said first regulator means.

7. The apparatus of claim 1 that further includes a support means for mounting the first and second flow regulators in a side by side relationship.

8. The apparatus of claim 4 that further includes a radially expanded shield means surrounding the main flow line below said injection port.

9. The apparatus of claim 1 wherein said control means includes a series of adjustable clamp means mounted in said flow lines.

10. A gravity flow path for administering fluids intravenously to a patient that includes:

a main flow line having a spike means at the top end thereof for coupling the line to a fluid container and an injection means at the bottom end thereof for intravenously administering fluid to a patient;

a burette connected into the main flow line having an air vent for allowing ambient air to enter the burette;

a main drip chamber connected to a bottom outlet to the burette for regulating the flow of fluid through the main line;

a shunt flow line connected into the main flow line by an upper connector located above the burette and by a lower connector located below the mini-drip chamber;

an adult drip chamber connected into the shunt line for regulating the flow of fluid through said shunt line whereby fluids can pass through said main line at a medically low flow rate and said shunt line at a medically high flow rate;

control means mounted in said main flow line that is operable to selectively enable one fluid to be administered or two fluids to be simultaneously administered, a first one-way check valve mounted in the main flow line between the mini-drip chamber and the lower connector;

a second one-way check valve mounted in the shunt flow line between the adult drip chamber and the lower connector; and a third one-way check valve mounted in the main flow line between the burette and the upper connection.

11. The apparatus of claim 10 that further includes control means for routing fluids through said lines.

12. The apparatus of claim 11 that further includes a second spike means connected into the main flow line above the upper connector for connecting a second fluid container to said main flow line.

13. The apparatus of claim 12 that further includes an injection port mounted in the main flow line below the lower connector.

14. The apparatus of claim 13 that further includes blood filter means mounted in the shunt line.

15. The apparatus of claim 14 that further includes means in the shunt line for removing the filter.

16. The apparatus of claim 10 that further includes a fourth one-way valve mounted in the main flow line between the spike means and the upper connector.

* * * * *